United States Patent [19]

Tachibana et al.

[11] Patent Number: 4,950,585

[45] Date of Patent: Aug. 21, 1990

[54] COUPLER FOR PHOTOGRAPHIC USE

[75] Inventors: Kimie Tachibana; Yutaka Kaneko, both of Hino, Japan

[73] Assignee: Konica Corporation, Tokyo, Japan

[21] Appl. No.: 227,753

[22] Filed: Aug. 3, 1988

[30] Foreign Application Priority Data

Aug. 18, 1987 [JP] Japan ................................. 62-203450
Aug. 18, 1987 [JP] Japan ................................. 62-203451

[51] Int. Cl.$^5$ ............................................. G03C 7/16
[52] U.S. Cl. .................................... 430/385; 430/384; 430/558
[58] Field of Search ................ 544/281; 430/558, 384, 430/385

[56] References Cited

U.S. PATENT DOCUMENTS 3,171,740  3/1965  Menzel et al. ....................... 430/385
4,639,415  1/1987  Kaneko et al. ....................... 430/558
4,828,969  5/1989  Takada et al. ....................... 430/558

FOREIGN PATENT DOCUMENTS 1282819  12/1961  France .
 375191   6/1962  Japan .
4018756   8/1965  Japan .

OTHER PUBLICATIONS

Auzzi et al., "2-Phenylpyrazolo [1,5-a]pyrimidin-7-Ones", J. Med. Chem. 1983, 26, 1706–1709.

Chu et al., "Ring Transformation Reactions of C-Nucleosides", J. Het. Chem. 1986, 23(1) pp. 349–352.
Derwent Japanese Patent Report, week R25 8/5/70, p. 4, Section B, No. 44709R.

Primary Examiner—Mukund J. Shah
Assistant Examiner—C. L. Cseh
Attorney, Agent, or Firm—Jordan B. Bierman

[57] ABSTRACT

A novel cyan color-forming coupler for photographic use is disclosed. The coupler has a improved fastness for heat, humidity, and has a chemical structure represented by the following Formula I;

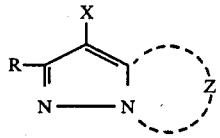

Formula I wherein Z is a group of non-metal atoms necessary for completing a nitrogen-containing six-member heterocyclic ring condensed with the pyrazole ring. The six-member ring may be substituted or not substituted provided that the six-member ring does not have be condensed with any ring other than the pyrazole ring; R represents a hydrogen atom or a substituent, and X represents a hydrogen atom or a substituent capable of being split off upon reaction with the oxidized product of a color developing agent.

7 Claims, No Drawings

COUPLER FOR PHOTOGRAPHIC USE

FIELD OF THE INVENTION

This invention relates to a novel coupler for photographic use intended to serve as a color photographic material and particularly to a coupler for photographic use which is capable of forming a dye image excellent in fastness against temperature, moisture and light.

BACKGROUND OF THE INVENTION

When a silver halide photographic light-sensitive material is exposed to light and is then color-developed, a dye is produced in the light-exposed areas of the light-sensitive material upon reaction of an oxidized aromatic primary amine color developing agent with a dye-forming coupler, so that a color image is formed.

Generally, in this photographic method, a color subtractive reproduction process is used to form each of yellow, magenta and cyan images.

For example, the couplers for photographic use for forming the above-mentioned yellow color images include acylacetanilide type couplers; those for forming the magenta color images include pyrazolone type, pyrazolobenzimidazole type, pyrazolotriazole type or indazolone type couplers; and those for forming the cyan color images include phenol type or naphthol type couplers; each of which is generally used.

It is a requirement of such dye images that they not be discolored even if they are exposed to light for a long time or are stored at a high temperature and a high humidity.

The phenol type and naphthol type couplers have been studied for use as the couplers for forming cyan dyes. However, they are as yet not quite satisfactory in spectral absorption characteristics, resistance to heat, moisture and light, and so forth. Aiming at solutions to these problems, there have been various proposals including those for selected substituents. But, no compound has yet been obtained to solve the above-mentioned problems.

SUMMARY OF THE INVENTION

It is an object of the invention to provide a coupler for photographic use which can be used as a color photographic material.

Another object of the invention is to provide a coupler for photographic use which is capable of forming cyan dye images having a hue not changeable when subjected to heat, moisture and light.

The above-mentioned objects of the invention can be accomplished with a coupler for photographic use which is represented by the following formula I.

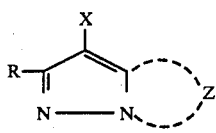

Formula I wherein Z is a group of non-metal atoms necessary to complete a nitrogen-containing 6-membered heterocyclic ring upon condensation-cyclization with the pyrazole ring, provided that the 6-membered ring may have a substituent, but is not condensed with other rings than the pyrazole ring; R represents a hydrogen atom or a substituent; and X represents a hydrogen atom or a substituent capable of being split off upon reaction with the oxidized product of a color developing agent.

DETAILED DESCRIPTION OF THE INVENTION

The couplers for photographic use, which relate to the invention, are so constituted as to form a 6-membered heterocyclic ring upon condensation with a pyrazole ring. There is no special limitation of the substituents represented by R; however, typical examples thereof include alkyl, aryl, anilino, acylamino, sulfonamido, alkylthio, arylthio, alkenyl, cycloalkyl etc. Also useful are a halogen atom, cycloalkenyl, alkinyl, heterocyclic, sulfonyl, sulfinyl, phosphonyl, acyl, carbamoyl, sulfamoyl, cyano, alkoxy, sulfonyloxy, aryloxy, heterocyclic oxy, siloxy, acyloxy, carbamoyloxy, amino, alkylamino, imido, ureido, sulfamoylamino, alkoxycarbonylamino, aryloxycarbonylamino, alkoxycarbonyl, aryloxycarbonyl, heterocyclic thio, thioureido, carboxy, hydroxy, mercapto, nitro, sulfonic acid, a spiro compound residual group, a bridged hydrocarbon compound residual group, etc.

The alkyl groups represented by R are preferably be those having 1 to 32 carbon atoms and they may be straight-chained or branched.

The aryl groups represented by R include, preferably, a phenyl group.

The acylamino groups represented by R include, for example, alkylcarbonylamino, arylcarbonylamino and so forth.

The sulfonamido groups represented by R include, for example, alkylsulfonylamino, arylsulfonylamino and so forth.

The alkyl and aryl components of the alkylthio and arylthio groups each represented by R include, for example, the alkyl and aryl groups each represented by the R.

The alkenyl groups represented by R include, for example, those having 2 to 32 carbon atoms; the cycloalkyl groups include, preferably, those having 3 to 12 carbon atoms and, more preferably, those having 5 to 7 carbon atoms; and the alkenyl groups may be straight-chained or branched.

The cycloalkenyl groups represented by R include, preferably, those having 3 to 12 carbon atoms and, more preferably, those having 5 to 7 carbon atoms.

The sulfonyl groups represented by R include, for example, alkylsulfonyl, arylsulfonyl and so forth;

The sulfinyl groups include, for example, alkylsulfinyl, arylsulfinyl and so forth;

The phosphonyl groups include, for example, alkylphosphonyl, alkoxyphosphonyl, aryloxyphosphonyl, arylphosphonyl and so forth;

The acyl groups include, for example, alkylcarbonyl, arylcarbonyl and so forth;

The carbamoyl groups include, for example, alkylcarbamoyl, arylcarbamoyl and so forth;

The sulfamoyl groups include, for example, alkylsulfamoyl, arylsulfamoyl and so forth;

The acyloxy groups include, for example, alkylcarbonyloxy, arylcarbonyloxy and so forth;

The carbamoyloxy groups include, for example, alkylcarbamoyloxy, arylcarbamoyloxy and so forth;

The ureido groups include, for example, alkylureido, arylureido and so forth;

The sulfamoylamino groups include, for example, alkylsulfamoylamino, arylsulfamoylamino and so forth;

The heterocyclic groups include, preferably, those having 5 to 7-membered ring and, typically, 2-furyl, 2-thienyl, 2-pyrimidinyl, 2-benzothiazolyl, 1-pyrrolyl, 1-tetrazolyl and so forth;

The heterocyclic oxy groups include, preferably, those having a 5 to 7-membered heterocyclic ring and, typically, 3,4,5,6-tetrahydropyranyl-2-oxy, 1-phenyltetrazole-5-oxy and so forth;

The heterocyclic thio groups include, preferably, those having 5 to 7-membered ring and, typically, 2-pyridylthio, 2-benzothiazolylthio, 2,4-diphenoxy-1,3,5-triazole-6-thio, and so forth;

The siloxy groups include, for example, trimethylsiloxy, triethylsiloxy, dimethylbutylsiloxy, and so forth;

The imido groups include, for example, succinimido, 3-heptadecyl succinimido, phthalimido, glutarimido and so forth;

The spiro compound residual groups include, for example, spiro [3,3] heptane-1-yl and so forth;

The bridged hydrocarbon compound residual groups include, for example, bicyclo [2,2,1] heptane-1-yl, tricyclo [3,3,1,1$^{3,7}$] decane-1-yl, 7,7-dimethyl-bicyclo [2,2,1] heptane-1-yl, and so forth.

The above-given groups are further allowed to have a substituent such as a ballast group including a long-chained hydrocarbon group, a polymer residual group and so forth.

X represents a group capable of being split off upon reaction with the oxidized product of a color developing agent. The groups include, for example, a halogen atom such as each atom of chlorine, bromine, fluorine and so forth and each group of alkoxy, aryloxy, heterocyclic oxy, acyloxy, sulfonyloxy, alkoxycarbonyloxy, aryloxycarbonyl, alkyloxalyloxy, alkoxyoxalyloxy, alkylthio, arylthio, heterocyclic thio, alkyloxythiocarbonylthio, acylamino, sulfonamido, nitrogen-containing heterocyclic ring bonded with an N atom, alkyloxycarbonylamino, aryloxycarbonylamino, carboxyl, and

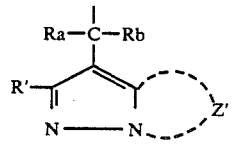

wherein R' is synonymous with the above-given R, Z' is synonymous with the above-given Z, and Ra and Rb each represent a hydrogen atoms, an aryl group, an alkyl group or a heterocyclic group, and so forth; and, preferably, a halogen atom. Among these groups, the particularly preferable ones include a hydrogen atom and a chlorine atom.

The preferably examples of the compounds represented by Formula I are represented by the following formula II.

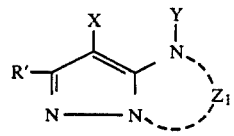

Formula II wherein $Z_1$ represents a group of non-metal atoms necessary to complete a nitrogen-containing 6-membered heterocyclic ring so as to contain at least one —NY— and at least one carbonyl group, upon condensation-cyclization with the pyrazole ring, provided that the 6-membered ring may have a substituent but may not be condensed with any other ring than the pyrazole ring; R and Y each represent a hydrogen atom or a substituent; and X represents a hydrogen atom or a substituent capable of being split off upon reaction with the oxidized product of a color developing agent.

The compounds represented by Formula II will now be described further in detail.

In Formula II, the nitrogen-containing 6-membered heterocyclic ring formed by $Z_1$ should preferably be those of either $6\pi$ or $8\pi$ electron system, which contains 1 to 4 nitrogen atoms including at least one —NY—. At least one carbonyl group contained in the 6-membered ring represents a group such as >C=O, >C=S and so forth; and R and X are synonymous with R and X denoted in Formula I, respectively.

In Formula II, Y represents a hydrogen atom or a substituent. The preferable substituents represented by Y are those capable of being split off from the abovementioned compounds upon reaction of the compounds of the invention with the oxidized product of a color developing agent. The substituents represented by Y include those capable of being split off under an alkaline condition such as described in Japanese Patent Publication Open to Public Inspection (hereinafter referred to as Japanese Patent O.P.I. Publication) No. 228444-1986 and so forth, those capable of coupling off upon reaction with the oxidized product of a color developing agent such as described in Japanese Patent O.P.I. Publication No. 133734-1981 and so forth. However, the preferably one represented by Y should be a hydrogen atom.

Among the compounds represented by Formula II, the most preferably examples should be the compounds represented by the following formula III or IV.

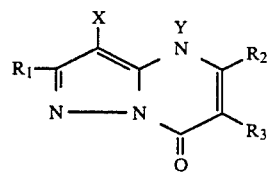

Formula III wherein $R_1$, $R_2$ and $R_3$ are synonymous with R denoted in Formula I; X is synonymous with X denoted in Formula I; and Y is synonymous with Y denoted in Formula II.

In Formula III, $R_2$ and $R_3$ are synonymous with R denoted in Formula I, however, $R_2$ cannot be a hydroxy group.

$R_2$ and $R_3$ preferably represent, for example, alkyl, aryl, carboxyl, oxycarbonyl, cyano, alkoxy, aryloxy, amino, amido, sulfonamido and so forth, atoms of hydrogen and halogen, and so forth.

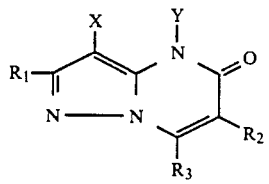

Formula IV wherein $R_1$, $R_2$ and $R_3$ each are synonymous with the R denoted in Formula I; and X and Y each are synonymous with X and Y denoted in Formula II, respectively; however, in the compounds represented by Formula IV, it is preferred that Y represents a hydrogen atom, that is to say, the compounds represented by the following Formula V.

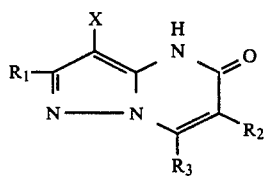

Formula V wherein $R_1$, $R_2$, $R_3$ and X each are synonymous with $R_1$, $R_2$, $R_3$ and X denoted in the compounds represented by Formula IV.

Next, the typical examples of the compounds of the invention will be given below. It is, however, to be understood that the invention shall not be limited thereto.

Examples of the compounds represented by Formula III

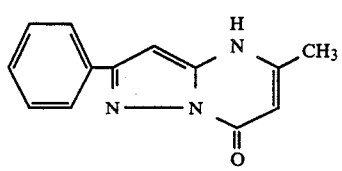

(1)

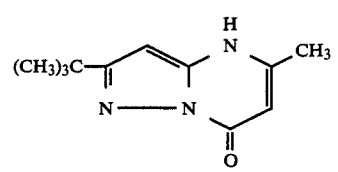

(2)

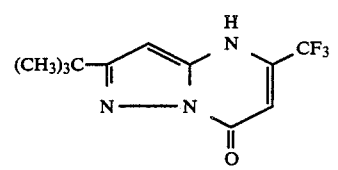

(3)

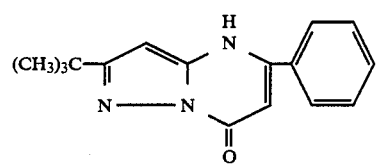

(4)

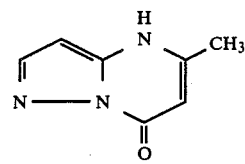

(5)

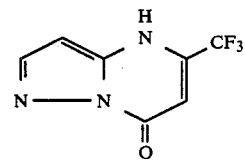

(6)

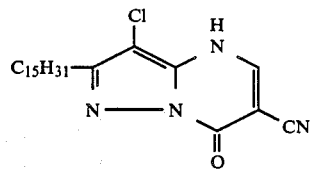

(7)

-continued
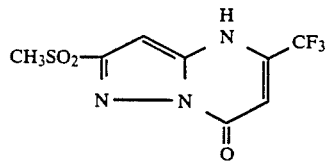(8)
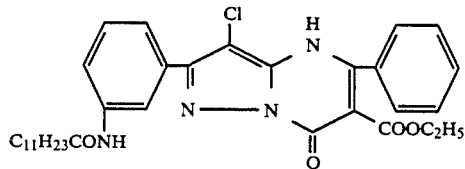(9)
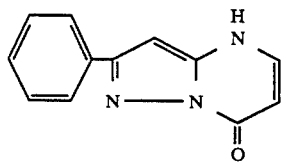(10)
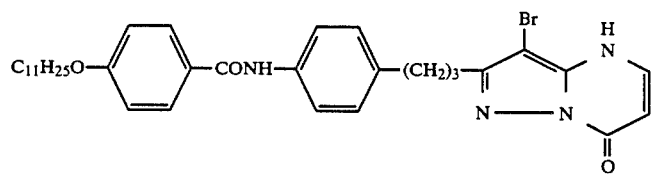(11)
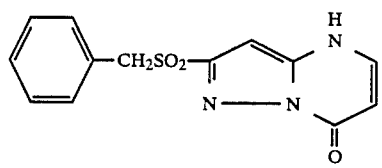(12)
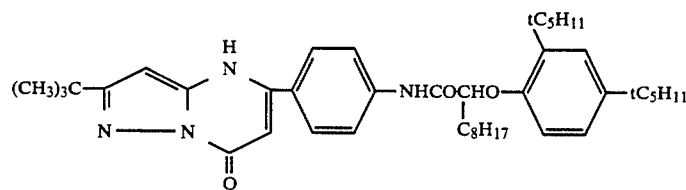(13)
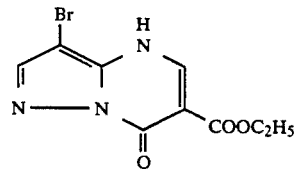(14)
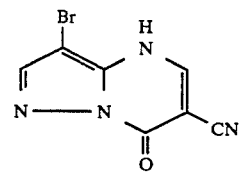(15)
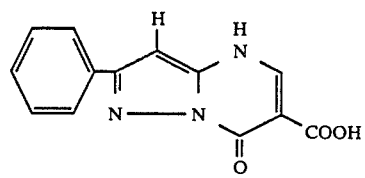(16)

-continued
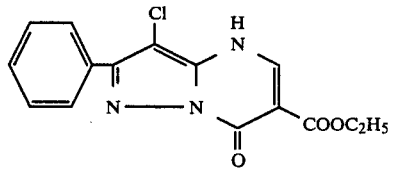 (17)
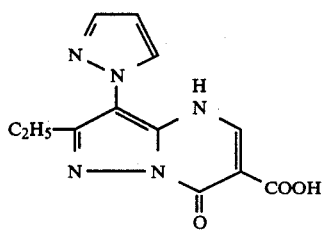 (18)
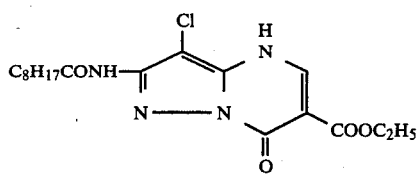 (19)
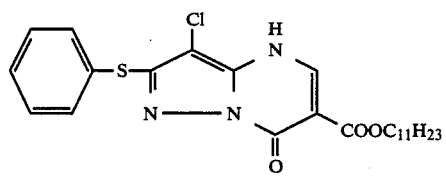 (20)
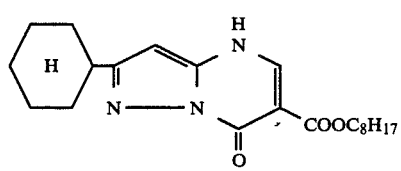 (21)
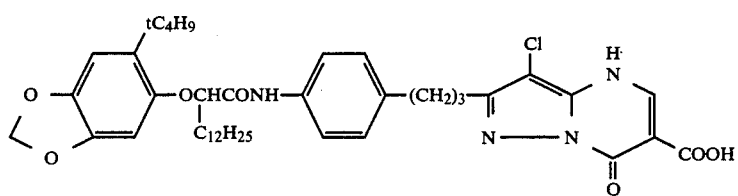 (22)
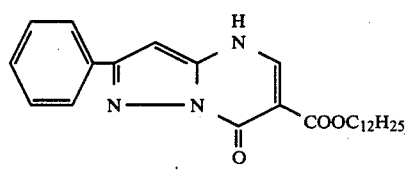 (23)
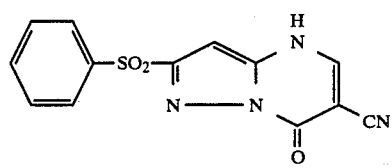 (24)
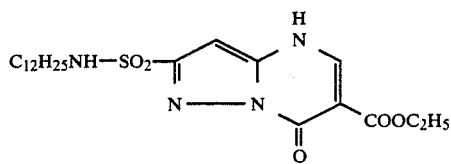 (25)

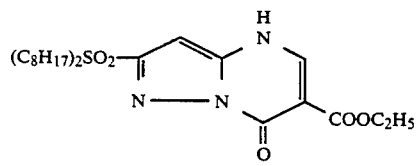
(26)
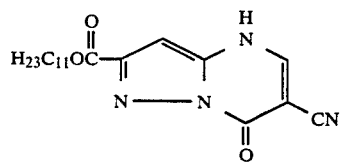
(27)
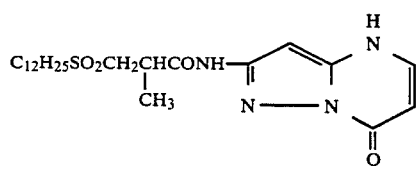
(28)
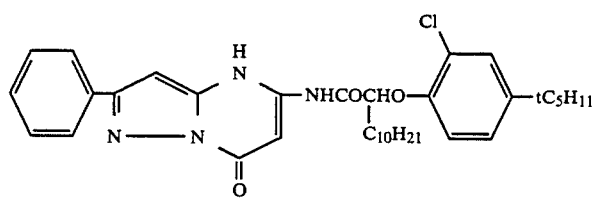
(29)
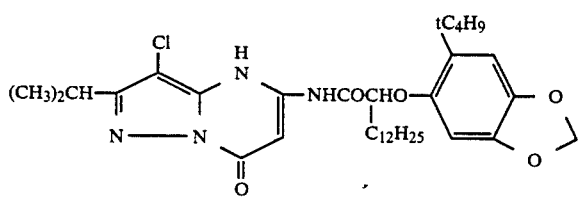
(30)
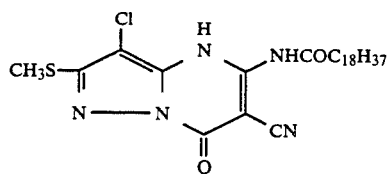
(31)
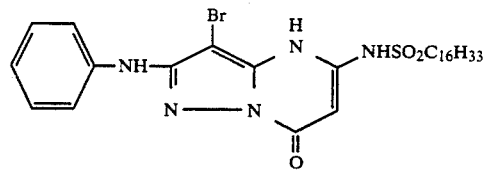
(32)
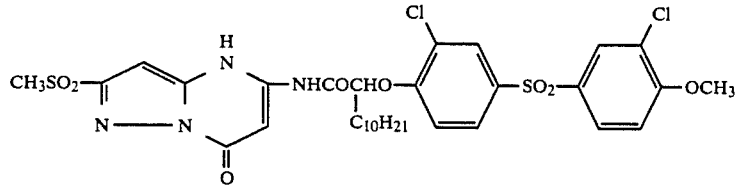
(33)
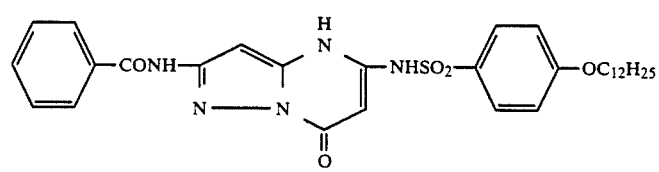
(34)

-continued
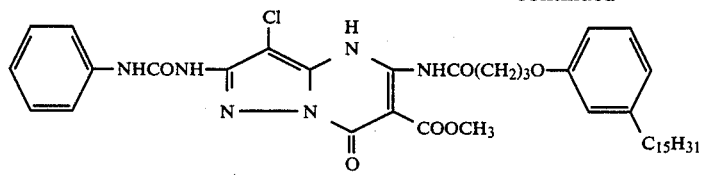 (35)
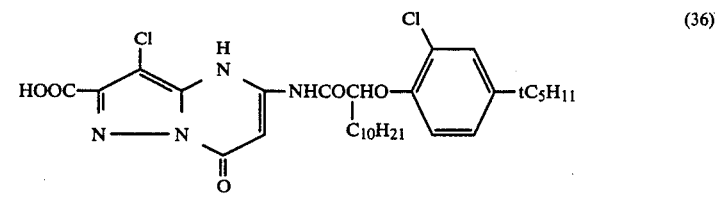 (36)
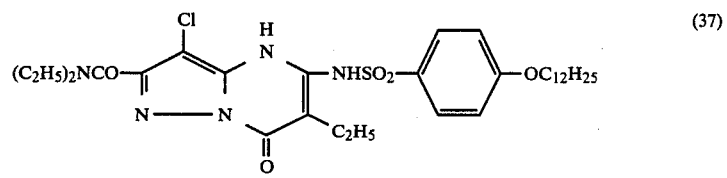 (37)
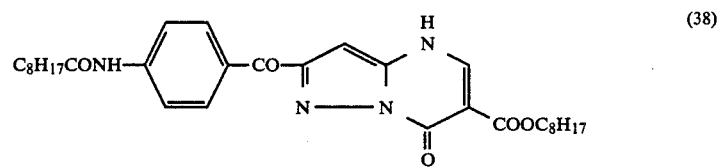 (38)
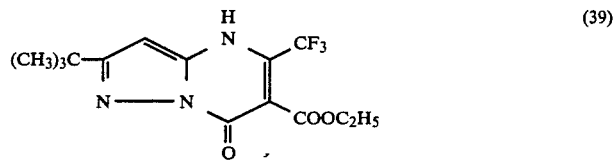 (39)
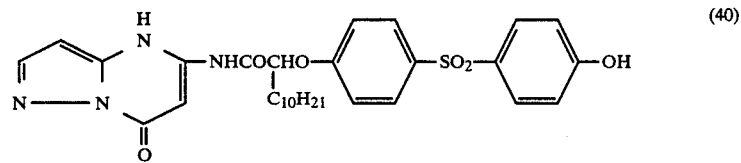 (40)
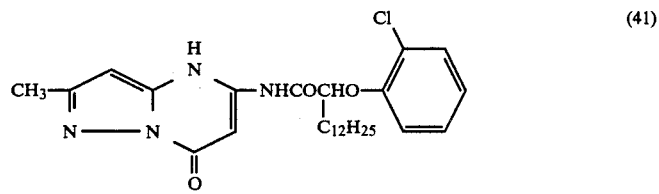 (41)
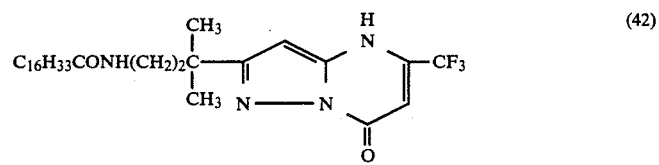 (42)
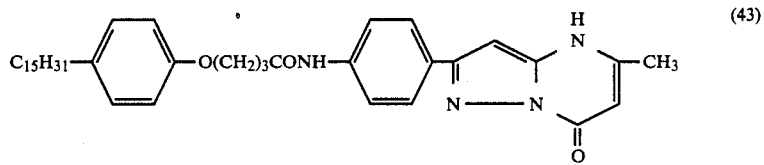 (43)

-continued
Examples of the compounds represented by Formula IV
(44)
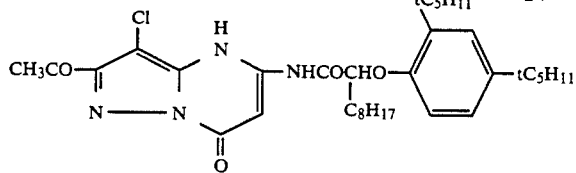
(45)
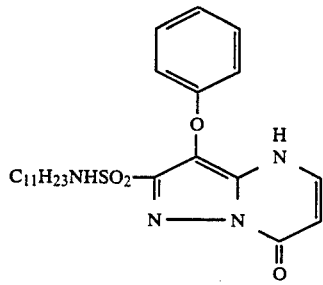
(46)
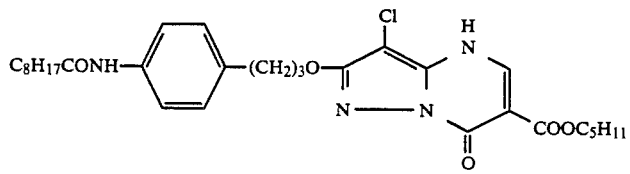
(47)
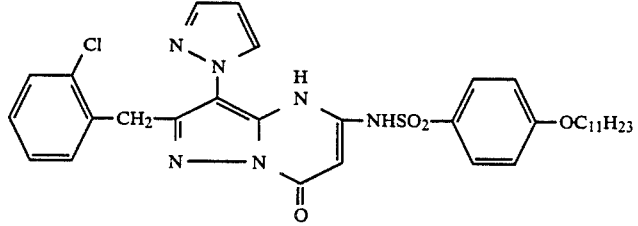
(48)
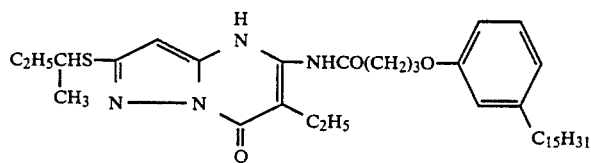

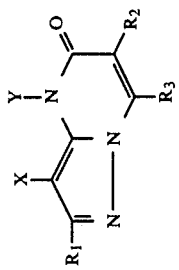
| No. | R₁ | R₂ | R₃ | R₂ | X |
|---|---|---|---|---|---|
| 49 | —CH₃ | H | H | H | Cl |
| 50 | —C₂H₅ | H | H | H | H |
| 51 | —C₁₅H₃₁ | H | H | H | Cl |
| 52 | ![p-dodecyloxyphenyl-NHSO₂-p-tolyl] | H | H | H | H |
| 53 | —CH(CH₃)(CH₂)₂NHCO(CH₂)₃O-(3-C₁₅H₃₁-phenyl) | H | H | H | Cl |
| 54 | p-SCH₂-phenyl-NHCOCH(C₆H₁₃)-(2,4-di-tC₅H₁₁-phenoxy) | H | H | H | Cl |
| 55 | m-SO₂-phenyl-NHSO₂C₁₁H₂₃ | H | H | H | H |
| 56 | p-NH-phenyl-OC₁₈H₃₇ | H | H | H | Br |
| 57 | —OC₁₂H₂₅ | H | H | H | Cl |
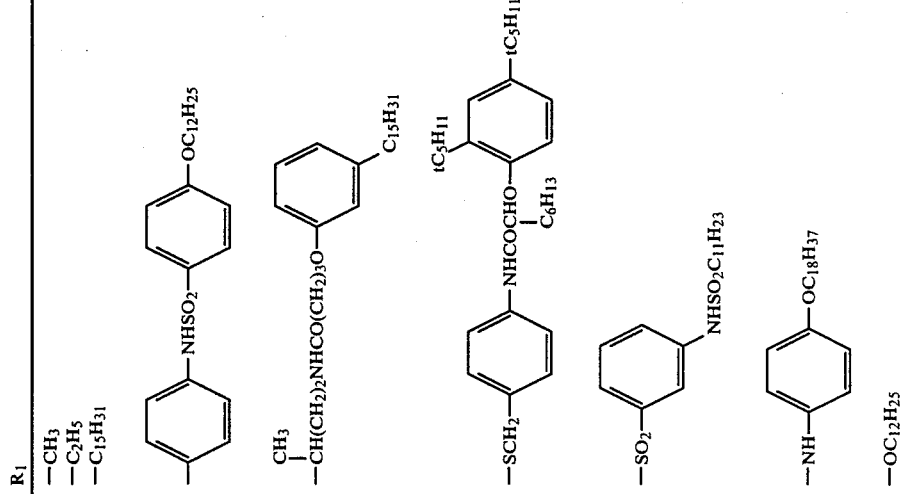

-continued
| No. | R₁ | R₂ | R₃ | X |
|---|---|---|---|---|
| 58 | ![structure with C₁₁H₂₃ phenyl]—NHCONH— | H | H | H |
| 59 | —CONHC₁₂H₂₅ | H | H | Cl |
| 60 | —SO₂N(C₈H₁₇)₂ | H | H | H |
| 61 | ![structure]—COCH₂—⟨C₆H₄⟩—NHCOC₁₃H₂₇ | H | H | Cl |
| 62 | H | H | —OH | H |
| 63 | H | H | —OC₁₁H₂₃ | H |
| 64 | —CH(CH₃)₂ | H | —OC₈H₁₇ | Cl |
| 65 | ![structure]—NHCOCHO—⟨benzodioxole tC₄H₉⟩ with C₁₂H₂₅ | H | —OCH₃ | Cl |
| 66 | ![structure]—SO₂CH₂—⟨C₆H₄⟩—OC₁₂H₂₅ | H | —OC₂H₅ | H |
| 67 | —C₁₂H₂₅ | H | —OCH₃ | H |
| 68 | —COOC₁₈H₃₇ | H | —OCH₃ | Cl |
| 69 | H | Cl | —CH₃ | Cl |
| 70 | —SCH₃ | Cl | —CH₃ | H |

-continued

[Structure: pyrazolone with substituents R1, X, and N-Y-N-C(=O)-C(R2)=C(R3)]

| No. | R1 | R2 | R3 | X |
|---|---|---|---|---|
| 71 | 4-OC12H25-C6H4-NHSO2- | Cl | —CH3 | H |
| 72 | 4-Cl-C6H4-NHSO2- | Cl | —CH3 | H |
| 73 | (CH3)2C(CH2SO2C18H37)- | Cl | —C2H5 | Cl |
| 74 | —C16H33 | H | —C(CH3)3 | —O— —CH3 |
| 75 | —NHC6H5 | Br | —C11H23 | H |
| 76 | 3-(NHCOC11H23)-C6H4- | Cl | —CH3 | H |
| 77 | 4-(OC11H23)-C6H4-SO2NH- | Cl | —CH3 | H |
| 78 | 4-C11H23-C6H4-CO- | Cl | —CH3 | H |
| 79 | H | H | —NHSO2C18H33 | Cl |

-continued

[Structure: pyrazolone with substituents Y-N(C=O)-C(R2)=C(R3)-N=N-C(R1)=C(X)-]

| No. | R₁ | R₂ | R₃ | X |
|---|---|---|---|---|
| 80 | —CH₃ | H | 2-tC₅H₁₁, 5-tC₅H₁₁ phenyl with —NHCOCHC₈H₁₇— | Cl |
| 81 | —CH(CH₃)CH₂O—C₆H₄—C₁₅H₃₁ | H | —NHCOC₄H₉ | H |
| 82 | —C(CH₃)₃ | H | 3-Cl, 4-OC₁₂H₂₅ phenyl-SO₂-phenyl-NHCOCHC₁₀H₂₁ with 3-Cl,4-OH | Cl |
| 83 | —C₁₆H₃₃ | H | —NHSO₂—C₆H₄—OC₁₂H₂₅ | H |
| 84 | —SO₂CH₂C₆H₅ | H | benzodioxole with tC₄H₉ and —NHCOCHC₁₂H₂₅ | H |
| 85 | —NHCOCH₃ | H | —NHSO₂—C₆H₄—C₁₈H₃₇ | Cl |

-continued

[Structure: pyrazole ring with substituents R1, X, and N-Y-C(=O)-C(R2)=CR3]

| No. | R1 | R2 | R3 | X |
|---|---|---|---|---|
| 86 | —NH—C6H5 | H | —NHCOCHO—C12H25 (2-Cl phenyl) | —S—C6H4—OCH3 (4-) |
| 87 | —OC2H5 | H | —NHCO(CH2)3O—C6H4—C15H31 (3-) | Cl |
| 88 | —C6H5 | H | —NHCOC11H23 | H |
| 89 | —SO2N(C3H7)2 | H | —NHSO2—C6H3(C8H17)(OC4H9) | H |
| 90 | —SO2NHC12H25 | H | —NHCO(CH2)3O—C6H4—C15H31 (3-) | Cl |
| 91 | —COOCH3 | H | —NHSO2C16H33 | pyrazol-1-yl |

-continued

[Structure: pyrazolone with R1, R2, R3, X, Y substituents]

| No. | R₁ | R₂ | R₃ | X |
|-----|----|----|----|---|
| 92 | —COCH₃ | H | ![phenyl with tC₅H₁₁ (ortho), tC₅H₁₁ (para), NHCOCHO-C₁₁H₂₃] | H |
| 93 | —CH₂—[phenyl-NHCOC₁₈H₃₇] | H | —NHCOC₂H₅ | Cl |
| 94 | —CH₃ | —C₂H₅ | [phenyl with OC₄H₉, C₈H₁₇, NHSO₂] | Cl |
| 95 | —C₆H₅ | —C₈H₁₇ | [methylenedioxyphenyl with tC₄H₉, NHCOCHO] | H |

Next, the typical synthesis examples of the compounds of the invention will be given below.

SYNTHESIS EXAMPLE 1

(Synthesis of Compound 10)

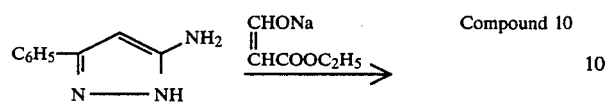

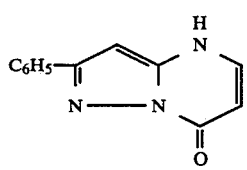

In 150 ml (0.1 mol) of dehydrated ethanol, 15.9 g of 3-phenyl-5-aminopyrazole and 21.1 g (0.1 mol) of sodium ethylformyl acetate were refluxed with heating for 30 minutes. The reacted solution was filtered with heating and 500 ml of water was added to the filtrate. The pH of the solution was adjusted to be pH 1 to pH 2 with diluted hydrochloric acid. The deposited crystals were filtered. After the crystals were washed with water and then with ether, they were recrystallized, so that 5.28 g (0.025 mols) of white needle-shaped crystal compound No. 10 were obtained.

Melting point: 330° C.

IR: 1670, 950, 790, 760, 770, 530 cm$^{-1}$, $^1$H-NMR(DMSO-d$_6$); 12.3s broad (1H,NH), 7.95m (2H,H ortho), 7.85d(1H,H$_5$, J$_{5,6}$=7.5 Hz), 7.45m(3H,H meta and para), 6.62s(1H,H$_3$), 5.71d(1H,H$_6$).

SYNTHESIS EXAMPLE 2

(Synthesis of Compound 17)

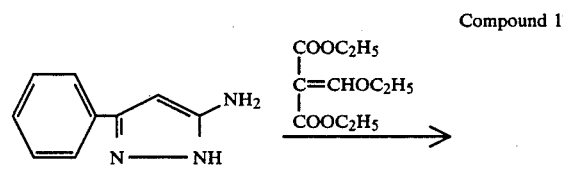

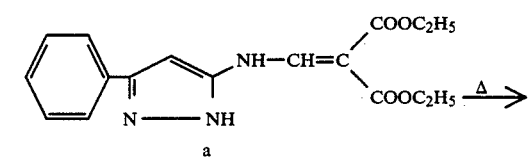

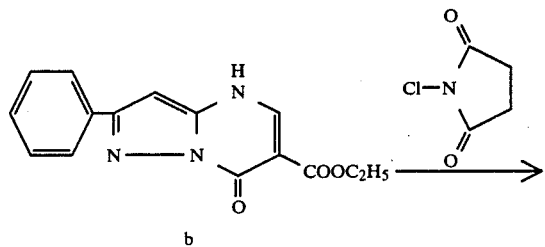

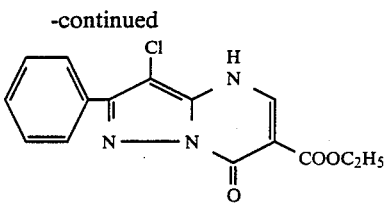

[Synthesis of a→]

In to 15.9 g (0.1 mol) of 3-phenyl-5-aminopyrazole, 43.2 g (0.2 mol) of diethylethoxymethylene malonate were added. The resultant oily mixture was stirred once and was then allowed to stand. The resulted solid matter was dissolved in 400 ml of ethanol and was then added with one liter of water gradually so as to filter the deposited white solid matter. The white solid matter was dissolved in benzene and was then recrystallized three times by adding cyclohexane gradually to crystallize it, so that 19.1 g (0.058 mol) of a in the form of white needle-shaped crystals were obtained.

Melting point: 103° to 105° C.

IR: 3380, 3250, 1730, 1680, 1660, 1640, 1620, 1240, 795, 740 cm$^{-1}$.

$^1$H-NMR(CDCl$_3$): 11.25 broad (1H,NH), 10.90d (1H,NH), 8.67d(1H,CH), 7.55m(2H,H ortho), 7.40m(3H, H meta and para), 6.25s(1H,H$_3$).

[a→b]

A reaction vessel containing 16.4 g (0.05 mol) of a was heated at a temperature of 180° C. in an oil bath until a was melted and was then cooled down. The resulted solid matter was filtrated and washed with ethanol. The solid matter was recrystallized with dimethylformamide, so that 1.5 g (0.023 mol) of light-yellowish white crystals b were obtained.

Melting point: 302° to 304° C.

IR: 1715, 1430, 1300, 1175, 790, 690, 610 cm$^{-1}$.

$^1$H-NMR(CF$_3$COOH): 9.10$_s$(1H,H$_5$), 8.00m(2H,H ortho), 7.67m(3H,H meta or para), 7.21$_s$(1H,H$_3$).

[b→Compound (17)]

b of 5.95 g (0.021 mol) were dissolved in 200 ml of chloroform and 3.0 g (0.022 mol) of N-chlorosuccinimide were then added thereto. The resulted solution was stirred for 30 minutes. The solvent was distilled off under reduced pressure and the remained matter was added with 150 ml each of ethyl acetate and water and was then extracted. After the ethyl acetate solution was dehydrated with magnesium sulfate, the extract was concentrated. The resulted concentrate was recrystallized with dimethylamide, so that 4.45 g (0.014 mol) of light-yellowish white needle-shaped crystals, i.e., Compound (17), was obtained.

FD-Mass-spectrum, M+317.

Elemental Analysis: Theoretical values, C: 56.71, H: 3.81, N: 13.23, Cl: 11.16. Measured values, C: 56.79, H: 3.75, N: 13.28, Cl: 11.22.

SYNTHESIS EXAMPLE 3

[Synthesis of Compound (16)]

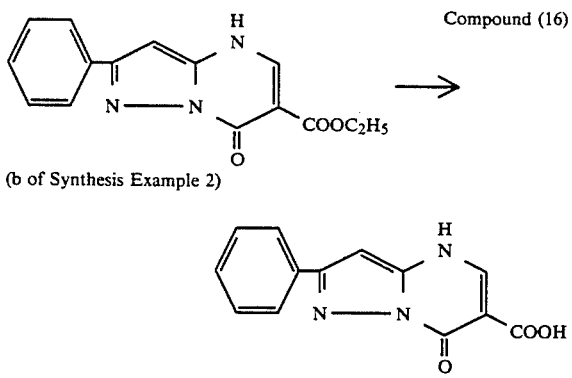

[Synthesis of compound 16]

In a water-containing alcohol suspension of sodium hydroxide 28.3 g (0.1 mol) of b which was synthesized in Synthesis Example 2 were heated until it was converted to a transparent solution and then refluxed. The reacted solution was adjusted to be pH 1 to 2 with diluted hydrochloric acid. The resulted white solid matter was filtered and was then recrystallized with dimethylformamide, so that 13.0 g (0.051 mol) of white needle-shaped crystals, i.e., Compound (16), were obtained.

Melting point: Decomposition was found at 328° to 330° C.

FD-Mass spectrum, M+255.

Elemental Analysis: Theoretical values, C: 61.18, N: 16.46, H: 3.55. Measured values, C: 61.05, N: 16.58, N: 3.50.

SYNTHESIS EXAMPLE 4

(Synthesis of Compound 29)

[Synthesis of a]

Both of 15.9 g (0.1 mol) of 5-amino-3-phenylpyrazole and 15.9 g (0.1 mol) of ethyl ester of 2-ethoxycarbonyacetamido were heated and reluxed for 20 hours in 200 ml of dehydrated ethanol. The resulted reacted solution was filtered while heating and the filtrate was cooled. The resulted precipitate was filtered and was washed with cooled ethanol. And then, the washed filtrate was recrystallized with a mixed solvent of dimethylformamide and water, so that 17.8 g (0.079 mols) of white needle-shaped crystals a were obtained.

Melting point of a: Not lower than 300° C.

$^1$H-NMR(DMSO-$d_6$): 11.2 to 12.0 broad(1H,NH), 7.8 to 8.0m (2H,$C_6H_5$), 7.3 to 7.5m (3H,$C_6H_5$), 6.62s (2H,$NH_2$), 6.4s (1H,H-3), 4.87s (1H,H-6).

Elemental analysis: Theoretical values: C: 63.71, H: 4.46, N: 24.76. Measure values: C: 63.95, H: 4.71, N: 24.52.

FD-Mass spectrum: M+226.

[a→Compound (29)]

One hundred milliliters of an ethyl acetate solution containing 31.2 g (0.075 mols) of b were added into 600 ml of an ethyl acetate solution containing 17.0 g (0.075 mols) of a and 7.8 g of triethylamine were further added. The resultant solution was stirred at room temperature for two hours and the deposited crystals were filtrated. The filtrates were washed with water and were then recrystallized with acetonitrile, so that 23.0 g (0.038 mols) of white needle-shaped crystals, Compound (29), were obtained.

FD-Mass spectrum: M+604.

Elemental analysis: Theoretical values: C: 69.46, H: 7.49, N: 9.26, Cl: 5.86. Measured values: C: 69.58, H: 7.55, N: 9.21, Cl: 5.72.

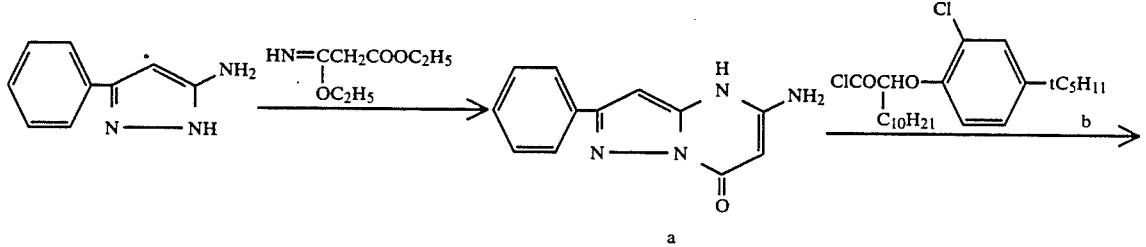

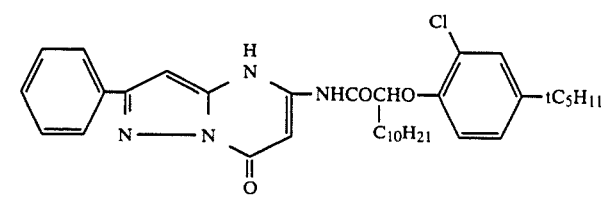

SYNTHESIS EXAMPLE 5

[Synthesis of Compound (34)]

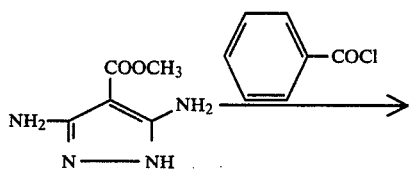

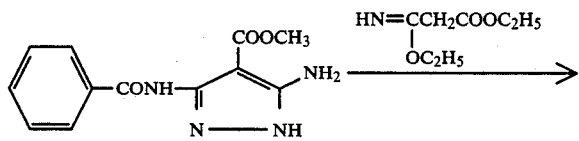

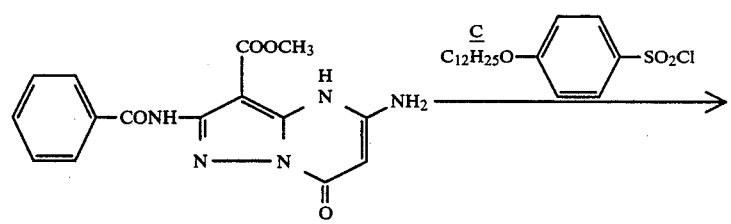

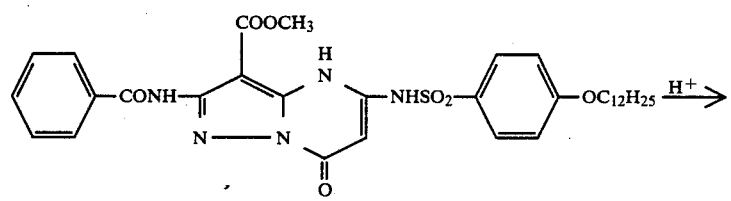

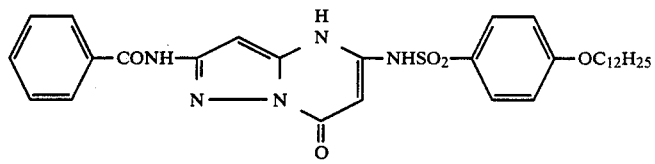

Compound (34)

Elemental analysis: Theoretical values: C: 55.05, H: 4.00, N: 21.40. Measure values: C: 54.95, H: 4.08, N: 20.35.

[Synthesis of a]

Into 500 ml of ethyl acetate were added with 15.6 g (0.1 mol) of methyl-3,5-diaminopyrazole-4-carboxylic acid, 14.1 g (0.1 mol) of benzoyl chloride and 15.2 g (0.15 mol) of triethylamine. The resulted solution was heated and refluxed for one hour. After the solution was cooled, the deposited crystals were filtered and then washed, so that 16.1 g (0.062 mol) of a were obtained.

[a→b]

As the materials of b, 16.0 g (0.062 mol) of a and 9.9 g (0.062 mol) of 2-ethoxycarbonylacetaoimidethyl ester were used. In the same manner as in [Synthesis of a] of the above-given Synthesis Example 4, b was synthesized by recrystallization with a mixed solvent of dimethylformamide and water, so that 13.1 g (0.040 mol) of light-yellow needle-shaped crystals b were obtained.

FD-Mass spectrum: $M^+327$

[b→d]

As the materials of d, 13.0 g (0.040 mol) of b and 14.4 g (0.040 mol) of c were used. In the same manner as in [a→Compound (29)] of Example 4, d was synthesized by recrystallizing with acetonitrile, so that 16.9 g (0.026 mol) of d were obtained.

[d→Compound (34)]

d of 15.6 g (0.024 mol) were dissolved in 720 ml of a mixed solution of acetic acid, sulfuric acid and water in a proportion of 100:25:5. The resulted solution was refluxed with heating for one hour. After the resulted matter was adjusted to be pH5 with an aqueous sodium hydroxide solution, it was extracted with ethyl acetate and, the solvents were dehydrated with magnesium sulfate and distilled off. The residues were recrystallized with acetonitrile, so that 8.3 g (0.014 mol) of light-yellowish white needle-shaped crystals, i.e., Compound (34), were obtained.

FD-Mass spectrum M+593.

Elemental analysis: Theoretical values: C: 62.71, H: 6.62, N: 11.80, S: 5.40. Measure values: C: 62.51, H: 6.69, N: 11.98, S: 5.29.

SYNTHESIS EXAMPLE 6

[Synthesis of Compound (41)]

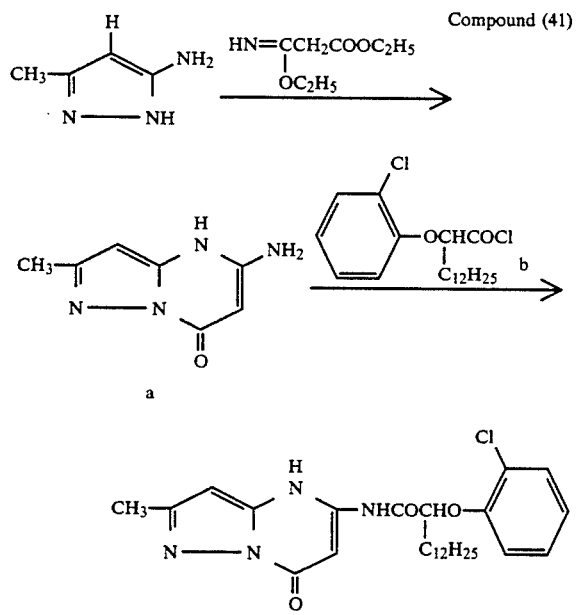

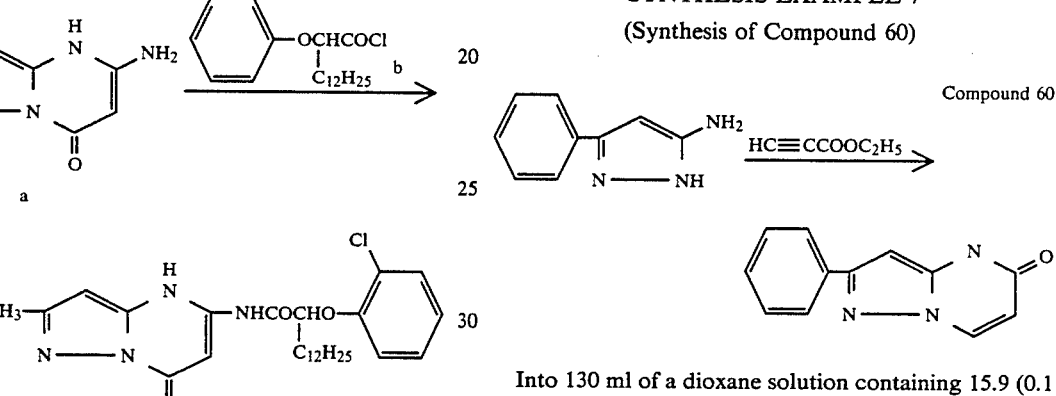

[Synthesis of a]

By making use of 9.7 g (0.1 mol) of 5-amino-3-methylpyrazole and 15.9 g (0.1 mol) of 2-ethoxycarbonylacetamido ethyl ester, a was synthesized in the same manner as in Synthesis of a of Example 4 and a was recrystallized with a mixed solvent of dimethylforamide and water, so that 13.1 g (0.08 mol) of white needle-shaped crystals of a were obtained.

Melting point: The decomposition was produced at a temperature of not lower than 300° C.

Elemental analysis: Theoretical values: C:51.21, N:34.13, H:4.91. Measured values: C:51.12, N:34.29, N:4.81.

FD-Mass spectrum M+164.

$^1$H-NMR(DMSO-d$_6$): 10.8 to 11.5 broad (1H,NH), 6.73 broad (2H,NH$_2$), 5.82s(1H,H-3), 4.78s(1H,H-6), 2.25s(3H,CH$_3$).

[a→Compound (41)]

By making use of 13.0 g (0.079 mol) of a and 29.5 g (0.079 mol) of b, Compound (41) was synthesized in the same manner as in [a→Compound (29)] of Synthesis Example 4 and was then recrystallized with acetonitrile, so that 21.5 g (0.043 mol) of white powder-like crystals, i.e., Compound (41), were obtained.

FD-Mass spectrum M+500.

Elemental analysis: Theoretical values: C:64.72, N:11.18, H:7.44, Cl:7.08. Measured values: C:64.92, N:11.21, H:7.38, Cl:7.00.

SYNTHESIS EXAMPLE 7

(Synthesis of Compound 60)

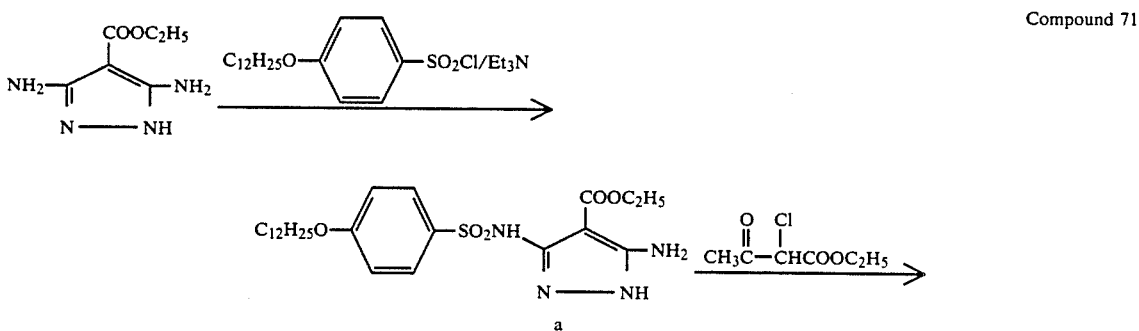

Into 130 ml of a dioxane solution containing 15.9 (0.1 mol) of 3-phenyl-5-aminopyrazole was added with 11.8 g (0.12 mol) of ethyl propionate and the resultant solution was refluxed with heating for 6 hours. The reacted solution was cooled and the deposited crystals were filtered. The crystals were recrystallized with ethanol, so that 13.1 g (0.062 mol) of white needle-shaped crystals, i.e., Compound 60, were obtained. The melting point: 284° to 286° C.

IR: 1660, 950, 810, 780, 840, 680.

$^1$H-NMR(DMSO-d$_6$): 12.12s(1H,NH), 8.50d(1H,H$_7$), 7.90m(2H,H ortho), 7.40m(3H,H meta and para), 6.28s(1H,H$_3$), 5.95d(1H,H$_6$).

SYNTHESIS EXAMPLE 8

(Synthesis of Compound 71)

-continued

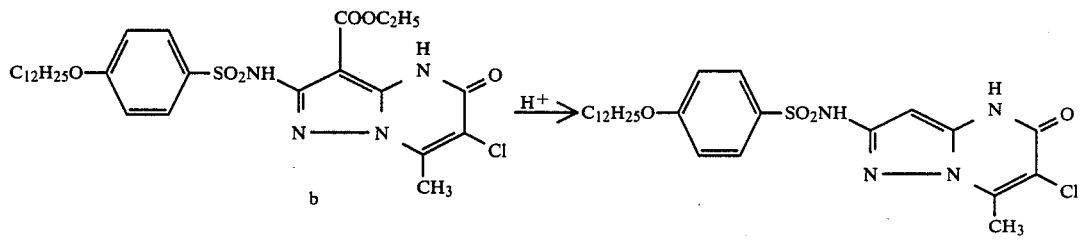

[Synthesis of a]

Into 500 ml of ethyl acetate were added with 17.0 g (0.1 mol) of ethyl-3,5-diaminopyrazole-4-carboxylic acid, 36.1 g (0.1 mol) of p-dodecaoxyphenylsulfonyl chloride and 15.2 g (0.15 mol) of triethylamine. The resultant solution was refluxed with heating for one hour. After it was cooled down, the deposited crystals were filtered and were then washed with water, so that 29.6 g (0.06 mol) of a were obtained.

[a→b]

In 600 ml of toluene, 29.1 g (0.059 mol) of a and 14.6 g (0.089 mol) of ethyl α-chloroaceto acetate were refluxed with heating for 6 hours and were then dehydrated.

The reacted solution was condensed under reduced pressure to obtain crude crystals. The crude crystals were recrystallized with ethanol, so that 16.1 g (0.027 mol) of white needle-shaped crystals, b, were obtained.

F-D mass spectrum 594.

Elemental analysis: Theoretical values: C:56.51, N:9.41, Cl:5.96, S:5.39. Measure values: C:56.70, N:9.49, Cl:5.85, S:5.29.

[b→Compound 71]

Into 130 ml of a mixed solvent of acetic acid, sulfuric acid and water (100:25:5), 15.4 g (0.026 mol) of b were dissolved. The resultant solution was refluxed with heating for one hour. The resultant matter was adjusted to be pH5 with sodium hydroxide and was then extracted with ethyl acetate. After the solvents were dehydrated with magnesium sulfate and were then distilled off. The residues were recrystallized with acetonitrile, so that 7.3 g (0.014 mol) of white needle-shaped crystals, i.e., Compound 71, were obtained.

F-d mass spectrum $M^+522$.

Elemental analysis: Theoretical values: C:57.40, H:6.74, N:10.71, Cl:6.78, S:6.13. Measure values: C:57.65, H:6.82, N:10.60, Cl:6.59, S:6.08.

SYNTHESIS EXAMPLE 9

(Synthesis of Compound 80)

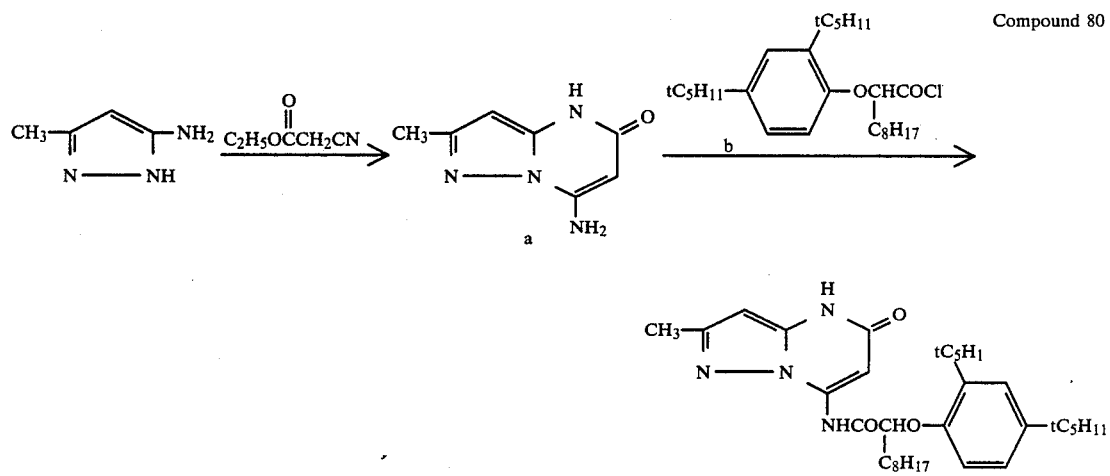

[Synthesis of a]

In 200 ml of dehydrated ethanol, 9.7 g (0.1 mol) of 5-amino-3-methylpyrazole and 11.3 g (0.1 mol) of ethyl cyanoacetate were refluxed with heating for 2.5 hours. After the reacted solution was cooled, the resulted precipitates were filtered and were then washed with cooled ethanol. The precipitates were recrystallized with a mixed solvent of dimethyl formamide and water, so that 10.0 g (0.061 mol) of white powder a were obtained.

F-D mass spectrum $M^+164$.

Elemental analysis: Theoretical values: C:51.21, N:34.13, H:4.91. Measure values: C:51.10, N:34.05, H:5.00.

[a→Compound 80]

Into 300 ml of an ethyl acetate solution containing 9.7 g (0.059 mol) of a were added with 80 ml of an ethyl acetate solution containing 25.0 g (0.059 mol) of b and, further, with 6.14 g of triethylamine. The resulted solution was stirred at room temperature for 2.5 hours and the deposited crystals were filtered. The crystals were washed with water and then recrystallized with acetonitrile, so that 16.5 g (0.030 mol) of white powder, i.e., Compound 80, were obtained.

F-D mass spectrum $M^+550$.

Elemental analysis: Theoretical values: C:71.96, N:10.17, H:9.15. Measured values: C:71.85, N:10.28, H:9.21.

As exemplified by the above-given synthesis examples 1 through 9, the compounds of the invention can be synthesized in an ordinary method by making use of a 3-substituted-5-aminopyrazole compound having a variety of substituents in the third position, as the raw material.

Usually, the couplers of the invention may be used in an amount within the range of from $1\times10^{-3}$ mol to 1 mol and, preferably, from $1\times10^{-2}$ mol to $8\times10^{-1}$ mol per mol of silver halide used.

The couplers of the invention are also allowed to be used with other kinds of couplers in combination.

To the couplers of the invention, it is similarly allowed to apply ordinary methods and techniques applicable to normal types of dye-forming couplers.

The couplers of the invention can also be used for color photographs finished in any color forming method. Such color forming methods include, more typically, a non-incorporated coupler type color forming method and an incorporated coupler type color forming method. When using the couplers of the invention in the non-incorporated coupler type color forming method, the couplers of the invention may be used by dissolving them in either an aqueous alkaline solution or an organic solvent such as alcohol or the like and then by adding them into a color developing solution.

When using the couplers of the invention as a material of color photographs finished in the incorporated coupler type color forming method, the couplers of the invention may be used by adding them into a photographic light-sensitive material.

Typically, it is preferable to use method such that the couplers of the invention are compounded into a silver halide emulsion and the emulsion is coated on a support to produce a color light-sensitive material. The couplers of the invention may be used in such a color photographic light-sensitive materials as color-negative and color-positive films, color-print papers and so forth.

The light-sensitive materials including the above-mentioned color-print papers, in which the couplers of the invention are used, may be those for monocolor or multi-color use. In such a multicolor light-sensitive material, the couplers of the invention may be in any layers thereof. It is, however, usual to incorporate the couplers into a red light-sensitive silver halide emulsion layer. Such multicolor light-sensitive materials have dye image forming component units which are sensitive to the three primary spectral color regions. Each of the component units may be comprised of a single or multiple emulsion layers sensitive to a certain spectral region. In a light-sensitive material, the component layers including the image forming component unit layer may be arranged in various orders as known in the art.

A typical multicolor light-sensitive material of the invention comprises a support carrying thereon a cyan dye image forming component unit comprising at least one red sensitive silver halide emulsion layer containing at least one cyan coupler of which at least one is the cyan coupler of the invention, a magenta dye image forming component unit comprising at least one green sensitive silver halide emulsion layer containing at least one magenta coupler and a yellow dye image forming component unit comprising at least one blue sensitive silver halide emulsion layer containing at least one yellow coupler.

The light-sensitive materials are also allowed to have additional layers such as a filter layer, an interlayer, a protective layer, a subbing layer and so forth. In order to incorporate the couplers of the invention into an emulsion, it is allowed to follow the conventionally known methods. For example, the couplers of the invention are dissolved independently or in combination in a high boiling organic solvent having a boiling point of not lower than 175° C. such as tricresyl phosphate, dibutyl phthalate or the like or in a low boiling solvent such as butyl acetate, butyl propionate or the like, or in the mixed solvent thereof if required. The resultant solution is mixed with an aqueous gelatin solution containing a surfactant and the mixture thereof is then emulsified by making use of a high-speed rotary mixer or a colloid-mil. Thereafter, the resultant dispersion is added to a silver halide emulsion, so that a silver halide emulsion applicable to the invention may be prepared.

To a light-sensitive material containing the coupler of the invention, the silver halide compositions which are preferably be applicable include, for example, silver chloride, silver chlorobromide or silver chloroiodobromide. The compositions thereof may also be a combined mixture of silver chloride and silver bromide or the like. When a silver halide emulsion is to be used in a color-print paper, for example, rapid developability is particularly required. The silver halide emulsion should, therefore, contain chlorine as the halide component of the silver halide. The particularly preferable silver halide compositions include silver chloride, silver chlorobromide or silver chloroiodobromide each having a silver chloride content of at least 1%.

The silver halide emulsions may be chemically sensitized by any known method, and it may also be optically sensitized to a desired wavelength range.

The silver halide emulsions may also be added with a compound which is known in the photographic art as an antifoggant or a stabilizer, to prevent fogging and/or to maintain photographic stability in the course of manufacturing, storing or processing a light-sensitive material.

The color light-sensitive materials containing the couplers of the invention may further include color-fog inhibitor, a dye image stabilizer, a UV absorbent, an antistatic agent, a matting agent, a surfactant and so forth, each of which is commonly used in light-sensitive materials.

For further details of these additives, reference is made to Research Disclosure, Vol. 176, pp. 22 to 31, Dec., 1978, for example.

With a color photographic light-sensitive material containing the couplers of the invention, an image may be formed through a color developing process which is well-known in the art.

The couplers relating to the invention are allowed to contain a color developing agent or its precursor in the hydrophilic colloidal layers of the light-sensitive materials so as to be processed in an alkaline activating bath.

The color photographic light-sensitive materials used therein the couplers of the invention may be color-developed, bleached and then fixed, provided that the bleaching step and the fixing step may be carried out at the same time.

After the fixing step, a washing step is commonly carried out. It is, however, permitted to carry out either a stabilizing step in place of the washing step, or the process combined with these two steps.

EXAMPLES

Next, the invention will be described further in detail with reference to the examples. It is, however, to be understood that the invention shall not be limited thereto.

EXAMPLE 1

The following layers were coated on a paper support laminated on the both sides with polyethylene, in order from the support side, so that Sample 1 of a red color light-sensitive material was prepared. Unless otherwise expressly stated, the amounts of the compounds added will be shown as an amount per square meter. (The amount of silver halide will be shown in terms of silver.)

Layer 1

An emulsion layer

The red-sensitive emulsion layer comprises 1.2 g of gelatin, 0.30 g of a red-sensitive silver chlorobromide emulsion (having a silver chloride content of 96 mol %), and $9.1 \times 10^{-4}$ mol of Comparative Cyan Coupler a dissolved in 1.35 g of dioctyl phosphate

Layer 2

A protective layer

The protective layer contained 0.50 g of gelatin. This layer also contained the sodium salt of 2,4-dichloro-6-hydroxy-s-triazine in an amount of 0.017 g per g of gelatin, as a hardener.

Next, Samples 2 through 15 of the invention were prepared in exactly the same manner as in Sample 1, except that Comparative Coupler a was replaced by the coupler indicated in Table 1 (of which the amount added was the same mol amount as that of Comparative Coupler a).

Thus prepared Samples 1 through 15 were exposed to light using a known method and were then processed in the following steps, respectively.

| Processing steps: | | |
|---|---|---|
| Color developing | 38° C. | 3 min. 30 sec. |
| Bleach-fixing | 38° C. | 1 min. 30 sec. |
| Stabilizing or washing | 25 to 30° C. | 3 min. |
| Drying | 75 to 80° C. | 2 min. |

In the above-given processing steps, the composition of each processing solution was as follows.

| Color developer: | |
|---|---|
| Benzyl alcohol | 15 ml |
| Ethylene glycol | 15 ml |
| Potassium sulfite | 2.0 g |
| Potassium bromide | 0.7 g |
| Sodium chloride | 0.2 g |
| Potassium carbonate | 30.0 g |
| Hydroxylamine sulfate | 3.0 g |
| Polyphosphoric acid (TPPS) | 2.5 g |
| 3-methyl-4-amino-N-ethyl-N-($\beta$-methanesulfonamidoethyl)aniline sulfate | 5.5 g |
| Fluorescent brightening agent (A 4,4'-diaminostilbenedisulfonic acid derivative) | 1.0 g |
| | 1.0 |
| Potassium hydroxide | 2.0 g |
| Add water to make a total of | 1 liter |
| Adjust pH to be | pH 10.20 |
| Bleach-fixer: | |
| Ferric ammonium ethylenediaminetetraacetate, dihydrate | 60 g |
| Ethylenediaminetetraacetate | 3 g |
| Ammonium thiosulfate (In a 70% solution) | 100 ml |
| Ammonium sulfite (In a 40% solution) | 27.5 ml |
| Adjust pH with potassium carbonate or glacial acetic acid to be | pH 7.1 |
| Add water to make a total of | 1 liter |
| Stabilizer: | |
| 5-chloro-2-methyl-4-isothiazoline-3-one | 1.0 g |
| Ethylene glycol | 10 g |
| Add water to make | 1 liter |

With respect to Samples 1 through 15 thus processed, the density of each sample was measured with a densitometer, Model KD-7 manufactured by Konishiroku Photo Ind. Co., Ltd. and, further, each of the samples was allowed to stand for 14 days in an atmosphere of a high temperature and a high humidity (at 60° C. and 80% RH); then the resistance against heat and moisture of dye images was determined.

Further, each of the samples was irradiated for 10 days by a Xenon Fade-o-meter and the density of the samples was measured and the light fastness thereof was determined. The results thereof are shown in Table 1; the heat resistance, moisture resistance and light fastness of the dye images are expressed by a percentage of the residual dye density obtained after the tests of resistance against heat, moisture and light to the initial density of 1.0.

Comparative Coupler a

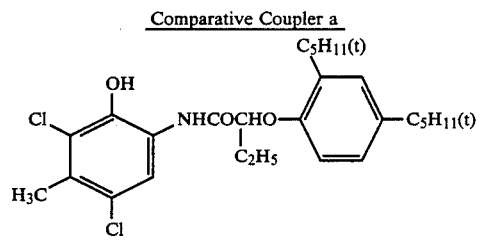

TABLE 1

| | | Residual ratio of dye (%) | |
|---|---|---|---|
| Sample No. | Coupler used | Heat/Moisture resistance | Light-fastness |
| 1 | Comp. a | 60 | 84 |
| 2 | Inv. 9 | 95 | 85 |
| 3 | Inv. 11 | 90 | 80 |
| 4 | Inv. 13 | 94 | 81 |
| 5 | Inv. 19 | 91 | 90 |
| 6 | Inv. 29 | 92 | 83 |
| 7 | Inv. 42 | 95 | 79 |
| 8 | Inv. 43 | 92 | 89 |
| 9 | Inv. 49 | 91 | 82 |
| 10 | Inv. 53 | 88 | 85 |
| 11 | Inv. 67 | 90 | 83 |
| 12 | Inv. 71 | 91 | 85 |
| 13 | Inv. 73 | 90 | 88 |
| 14 | Inv. 82 | 94 | 85 |
| 15 | Inv. 88 | 93 | 82 |

As is obvious from the results shown in Table 1, the couplers of the invention are high in dye residual ratio, excellent in both heat and moisture resistance without degradation in light-fastness, as compared to the sample which used the comparative coupler.

EXAMPLE 2

Onto a subbed triacetate film support was coated with each of the following layers in order from the support, so that a red color light-sensitive material sample No. 16 was prepared. The amount of each compound added is expressed in terms of the amount added per square meter unless otherwise expressly stated. (The amount of silver halide added will be expressed in terms of silver.)

Layer 1

An emulsion layer

The red-sensitive emulsion layer comprises 1.3 g of gelatin, 1.5 g of a red-sensitive silver iodobromide emulsion (having a silver iodide content of 4 mol %), and $8.0 \times 10^{-4}$ mol of Comparative Cyan Coupler b dissolved in 1.1 g of tricresyl phosphate

Layer 2

A protective layer

The protective layer contains 1.5 g of gelatin. This layer also included the sodium salt of 2,4-dichloro-6-hydroxy-s-triazine in an amount of 0.017 g per g of gelatin, as a hardener.

Next, Samples 17 through 29 of the invention were prepared in exactly the same manner as Sample 16, except that Comparative Coupler b was replaced by the coupler indicated in Table 2 (of which the amount added was the same mol amount as that of Comparative Coupler b).

Thus prepared film samples were exposed to light in a known method and were then color developed in the following color processing steps, respectively.

Comparative Coupler b

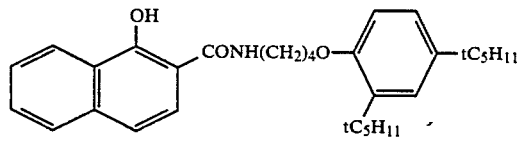

| Processing steps: Processing temperature at 38° C. | |
|---|---|
| | Processing time |
| Color developing | 3 min. 15 sec. |
| Bleaching | 6 min. 30 sec. |
| Washing | 3 min. 15 sec. |
| Fixing | 6 min. 30 sec. |
| Washing | 3 min. 15 sec. |
| Stabilizing | 1 min. 30 sec. |
| Drying | |

In the above-given processing steps, the composition of each processing solution was as follows.

| Color developer: | |
|---|---|
| 4-amino-3-methyl-N-ethyl-N-(β-hydroxyethyl)aniline sulfate | 4.75 g |
| Sodium sulfite, anhydrous | 4.25 g |
| Hydroxyamine ½ sulfate | 2.0 g |
| Potassium carbonate, anhydrous | 3.75 g |
| Sodium bromide | 1.3 g |
| Trisodium nitrilotriacetate, monohydrate | 2.5 g |
| Potassium hydroxide | 1.0 g |
| Add water to make | 1 liter |
| Adjust pH with sodium hydroxide to be | pH 10.6 |
| Bleaching solution: | |
| Ferric-ammonium ethylenediaminetetraacetate | 100.0 g |
| Diammonium ethylenediaminetetraacetate | 10.0 g |
| Ammonium bromide | 150.0 g |
| Glacial acetic acid | 10.0 g |
| Add water to make | 1 liter |
| Adjust pH with aqueous ammonia to be | pH 6.0 |
| Fixer: | |
| Ammonium thiosulfate | 175.0 g |
| Sodium sulfite, anhydrous | 8.0 g |
| Sodium metasulfite | 2.3 g |
| Add water to make | 1 liter |
| Adjust pH with acetic acid to be | pH 6.0 |
| Stabilizer: | |
| Formalin (at 37 wt %) | 1.5 ml |
| Koniducks (manufactured by Konishiroku Photo Ind. Co., Ltd.) | 7.5 ml |
| Add water to make | 1 liter |

With respect to Samples 16 through 29 thus processed, the density of cyan images formed on each sample was measured with a densitometer, Model KD-7 manufactured by Konishiroku Photo Ind. Co., Ltd. and, further, each of the samples was allowed to stand for 14 days in an atmosphere of a high temperature and a high humidity (at 60° C. and 80% RH) and, then, the resistance against heat and moisture of dye images was determined.

Further, each of the samples was irradiated for 10 days by a Xenon Fade-o-meter and, then, the density of the samples was measured and the light fastness thereof was determined.

The results thereof are shown in Table 2 the heat resistance, moisture resistance and light fastness of dye images are expressed by a percentage of the residual dye density obtained after the tests of resistance against heat, moisture and light to the initial density of 1.0.

TABLE 2

| | | Residual ratio of dye (%) | |
|---|---|---|---|
| Sample No. | Coupler used | Heat/Moisture resistance | Light-fastness |
| 16 | Comp. b | 71 | 80 |
| 17 | Inv. 25 | 91 | 85 |
| 18 | Inv. 27 | 92 | 86 |
| 19 | Inv. 33 | 85 | 83 |
| 20 | Inv. 37 | 91 | 85 |
| 21 | Inv. 38 | 92 | 84 |
| 22 | Inv. 44 | 90 | 81 |
| 23 | Inv. 55 | 84 | 80 |
| 24 | Inv. 59 | 88 | 82 |
| 25 | Inv. 68 | 92 | 80 |
| 26 | Inv. 78 | 86 | 83 |
| 27 | Inv. 84 | 93 | 85 |
| 28 | Inv. 90 | 91 | 82 |
| 29 | Inv. 92 | 89 | 85 |

As is obvious from the results shown in Table 2 the couplers of the invention are high in dye residual ratio, excellent in both heat and moisture resistance without degradation in light-fastness, as compared to the sample used therein the comparative coupler.

EXAMPLE 3

Onto a triacetyl cellulose film support was coated with each of the following layers in order from the support, so that red color light-sensitive reversal photographic material samples No. 30 through No. 40 were prepared.

Layer 1

An emulsion layer

The red-sensitive emulsion layer comprises 1.4 g of gelatin, 0.5 g of a red-sensitive silver chlorobromide emulsion (having a silver chloride content of 96 mol %), and $9.1 \times 10^{-4}$ mol of the coupler dissolved in 1.5 g of dibutyl phthalate.

Layer 2

A protective layer

The protective layer contains 0.5 g of gelatin. This layer also included the sodium salt of 2,4-dichloro-6-hydroxy-s-triazine in an amount of 0.017 g per g of gelatin, as a hardener.

Thus prepared samples were exposed to light in an ordinary method and were then developed in the following steps.

| Reversal Processing Steps: | | |
|---|---|---|
| Step | Time | Temperature |
| First developing | 6 min. | 38° C. |
| Washing | 2 min. | 38° C. |
| Reversing | 2 min. | 38° C. |
| Color developing | 6 min. | 38° C. |
| Adjusting | 2 min. | 38° C. |
| Bleaching | 6 min. | 38° C. |
| Fixing | 4 min. | 38° C. |
| Washing | 4 min. | 38° C. |
| Stabilizing | 1 min. | 38° C. |
| Drying | | At an ordinary temperature |

The compositions of the processing solutions used were as follows.

| First developer: | |
|---|---|
| Sodium tetrapolyphosphate | 2 g |
| Sodium sulfite | 20 g |
| Hydroquinone monosulfonic acid | 30 g |
| Sodium carbonate, monohydrate | 30 g |
| 1-phenyl-4-methyl-4-hydroxymethyl-3-pyrazolidone | 2 g |
| Potassium bromide | 2.5 g |
| Potassium thiocyanate | 1.2 g |
| Potassium iodide (in a 0.1% solution) | 2 ml |
| Add water to make | 1000 ml |
| Reversing solution: | |
| Hexasodium nitrilotrimethylene phosphonate | 3 g |
| Stannous chloride, dihydrate | 1 g |
| p-aminophenol | 0.1 g |
| Sodium hydroxide | 5 g |
| Glacial acetic acid | 15 ml |
| Add water to make | 1000 ml |
| Color developer: | |
| Sodium tetrapolyphosphate | 2 g |
| Sodium sulfite | 7 g |
| Tertiary sodium phosphate, 12 hydrate | 36 g |
| Potassium bromide | 1 g |
| Potassium iodide (in a 0.1% solution) | 90 ml |
| Sodium hydroxide | 3 g |
| Citrazinic acid | 1.5 g |
| N-ethyl-N-($\beta$-methanesilfonamidoethyl)-3-methyl-4-aminoaniline sulfate | 11 g |
| Ethylenediamine | 3 g |
| Add water to make | 1000 ml |
| Adjusting solution: | |
| Sodium sulfite | 12 g |
| Sodium ethylenediaminetetra-acetate, dihydrate | 8 g |
| Thioglycerol | 0.4 ml |
| Glacial acetic acid | 3 ml |
| Add water to make | 1000 ml |
| Bleaching solution: | |
| Sodium ethylenediaminetetra-acetate, dihydrate | 2.0 g |
| Ferric ammonium ethylenediamine-tetraacetate, dihydrate | 120.0 g |
| Potassium bromide | 100.0 g |
| Add water to make | 1000 ml |

| -continued | |
|---|---|
| Fixer: | |
| Ammonium thiosulfate | 80.0 g |
| Sodium sulfite | 5.0 g |
| Sodium bisulfite | 5.0 g |
| Add water to make | 1000 ml |
| Stabilizer: | |
| Formalin (at 37 wt %) | 5.0 ml |
| Koniducks (manufactured by Konishiroku Photo Ind. Co., Ltd.) | 5.0 ml 5.0 |
| Add water to make | 1000 ml |

With respect to each of the samples thus processed, the resistance against heat and moisture and light-fastness of the cyan dye images was examined in the same manner as in Example 2. The results thereof are shown in Table 3.

TABLE 3

| | | Residual ratio of dye (%) | |
|---|---|---|---|
| Sample No. | Coupler used | Heat/Moisture resistance | Light-fastness |
| 30 | Comp. a | 61 | 85 |
| 31 | Inv. 7 | 92 | 89 |
| 32 | Inv. 23 | 94 | 87 |
| 33 | Inv. 28 | 91 | 84 |
| 34 | Inv. 30 | 93 | 86 |
| 35 | Inv. 32 | 92 | 85 |
| 36 | Inv. 51 | 91 | 82 |
| 37 | Inv. 64 | 90 | 84 |
| 38 | Inv. 76 | 88 | 83 |
| 39 | Inv. 81 | 90 | 83 |
| 40 | Inv. 85 | 93 | 84 |

As is obvious from the results shown in Table-3, the couplers of the invention are high in dye residual ratio, excellent in both heat and moisture resistance and without degradation in light-fastness, as compared to the sample used therein the comparative coupler.

In conclusion, it is found that the dye images formed with the couplers of the invention are resistant to heat, moisture and light.

What is claimed is:

1. A method of forming a photographic dye image, said method comprising;

imagewise exposing to light, a silver halide photographic light-sensitive material comprising a support having thereon a silver halide emulsion layer containing a coupler represented by the following formula:

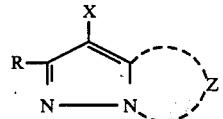

Formula I wherein Z is a group of non-metal atoms necessary to complete a nitrogen-containing six-member heterocyclic ring condensed with the pyrazole ring, said six-member ring being optionally substituted; provided that said six-member ring is not condensed with any ring other than said pyrazole ring; R represents a hydrogen atom or a substituent, and X represents a hydrogen atom or a substituent capable of splitting off upon reaction with an oxidized product of a color developing agent and;

developing said silver halide photographic light-sensitive material with a color developer containing a color developing agent.

2. The method of claim 1 wherein said coupler is represented by the following formula:

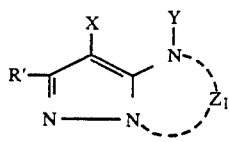

Formula II wherein $Z_1$ represents a group of non-metal atoms necessary to complete a nitrogen-containing six-member ring condensed with the pyrazole ring of Formula II, said six-member ring containing an -NY- group and a carbonyl group, and not being condensed with any ring other than said pyrazole ring; Y represents a hydrogen atom or a substituent; and R and X are the same as in Formula I.

3. The method of claim 2 wherein said coupler is represented by the following formula:

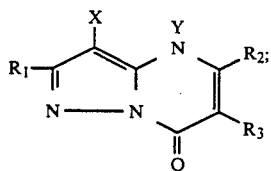

Formula III wherein $R_1$ $R_2$ and $R_3$ are the same as R denoted in Formula I, provided that $R_2$ is not a hydroxy group; and X and Y are the same as defined in Formula II.

4. The method of claim 2 wherein said coupler is represented by the following formula:

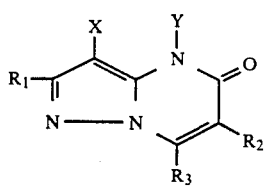

Formula IV wherein $R_1$, $R_2$, and $R_3$ are the same as R of Formula I, and X and Y are the same as defined in Formula II.

5. The method of claim 4 wherein said coupler is represented by the following formula:

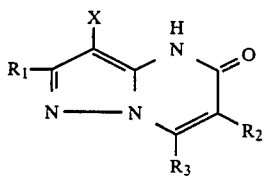

Formula V wherein $R_1$, $R_2$, $R_3$ and X are the same as defined in Formula IV.

6. The method of claim 1 wherein said coupler is present in said silver halide emulsion layer in an amount of $1 \times 10^{-3}$ to 1 mol per mol of silver halide.

7. The method of claim 6 wherein said coupler is present in said silver halide emulsion layer in an amount of from $1 \times 10^{-2}$ to $8 \times 10^{-1}$ mol per mol of silver halide.

* * * * *